United States Patent [19]

MacKenzie

[11] Patent Number: 5,351,689
[45] Date of Patent: Oct. 4, 1994

[54] METHOD AND APPARATUS FOR LOW DOSE ESTIMATES OF BONE MINERALS IN VIVO GAMMA RAY BACKSCATTER

[75] Inventor: Innes MacKenzie, Guelph, Canada

[73] Assignee: University of Guelph, Guelph, Canada

[21] Appl. No.: 112,590

[22] Filed: Aug. 26, 1993

Related U.S. Application Data

[62] Division of Ser. No. 762,326, Sep. 18, 1991.

[30] Foreign Application Priority Data

Sep. 18, 1990 [GB] United Kingdom ............ 9020353.0

[51] Int. Cl.⁵ ..................... A61B 6/00; G01N 23/203; G01T 1/00
[52] U.S. Cl. ................................ 128/653.1; 128/659; 250/363.01; 378/54; 378/86; 378/88; 378/89
[58] Field of Search ............... 128/653.1, 659; 378/54, 378/55, 86, 88, 89; 250/363.01, 370.09; 600/1, 7

[56] References Cited

U.S. PATENT DOCUMENTS

| | | | |
|---|---|---|---|
| 2,559,793 | 7/1951 | Pregel | 600/7 |
| 4,506,157 | 3/1985 | Keller | 128/653.1 |
| 4,829,549 | 5/1989 | Vogel et al. | 128/653.1 |
| 4,887,604 | 12/1989 | Shefer et al. | 128/654 |
| 4,986,273 | 1/1991 | O'Neill et al. | 128/653.1 |
| 5,003,980 | 4/1991 | Loo et al. | 378/89 |
| 5,029,337 | 7/1991 | MacKenzie et al. | 378/89 |
| 5,068,883 | 11/1991 | DeHaan et al. | 378/86 |
| 5,099,504 | 3/1992 | Pettit | 378/56 |
| 5,148,455 | 9/1992 | Stein | 378/55 |
| 5,150,395 | 9/1992 | Kosanetzky et al. | 378/86 |
| 5,151,598 | 9/1992 | Denen | 128/654 |
| 5,165,410 | 11/1992 | Warne et al. | 378/55 |

OTHER PUBLICATIONS

Canadian Journal of Physics, vol. 67, No. 8 (1989), pp. 821–826 entitled: "Nondestructive analysis of thick target specimens by gamma ray backscatter" by I. K. MacKenzie.

Bone and Mineral, 5 (1988) pp. 35–38 entitled: "The clinical relevance of calcaneus bone mineral measurements: a review" by John Max Vogel, Richard D. Wasnick, and Philip D. Ross.

Phys. Med. Biol., vol. 34, No. 5 (1989) pp. 543–572 entitled: "Methods of bone mineral measurement" by P. Tothill.

*Primary Examiner*—K. M. Pfaffle
*Attorney, Agent, or Firm*—Thomas R. Vigil

[57] ABSTRACT

A radioactive source holder for use with a NaI (TI) spectrometer for obtaining very low dose estimates in bone minerals in vivo, comprising a molybdenum tube, a gold insert within the tube, a blind hole within the insert for receiving the radioactive source, and an inner tube inserted into the blind hole for directing radiation from the source in a narrow cone, whereby the directing of radiation in the narrow cone minimizes spectrometer response to radiation which has been scattered by soft tissue overlying a bone.

7 Claims, 3 Drawing Sheets

FIG. 1B
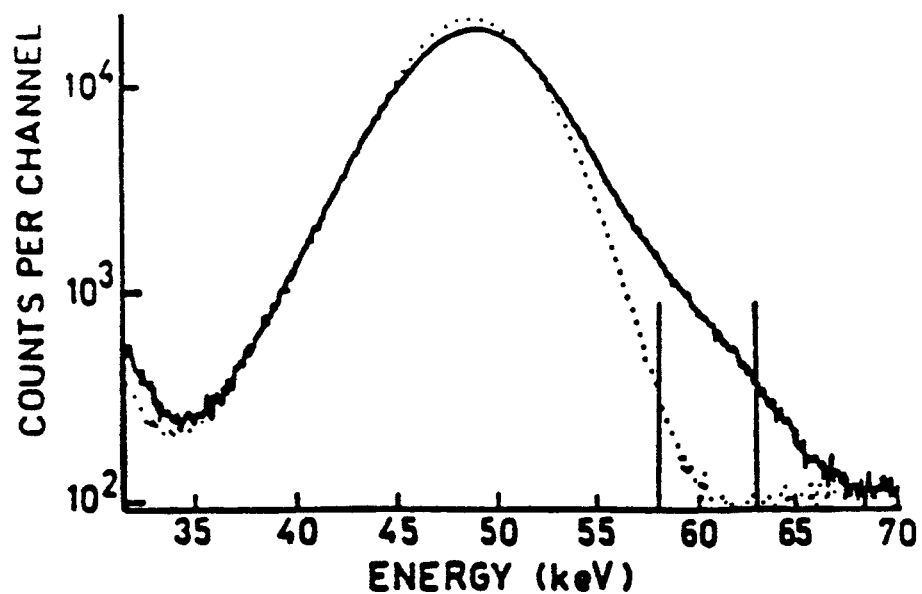
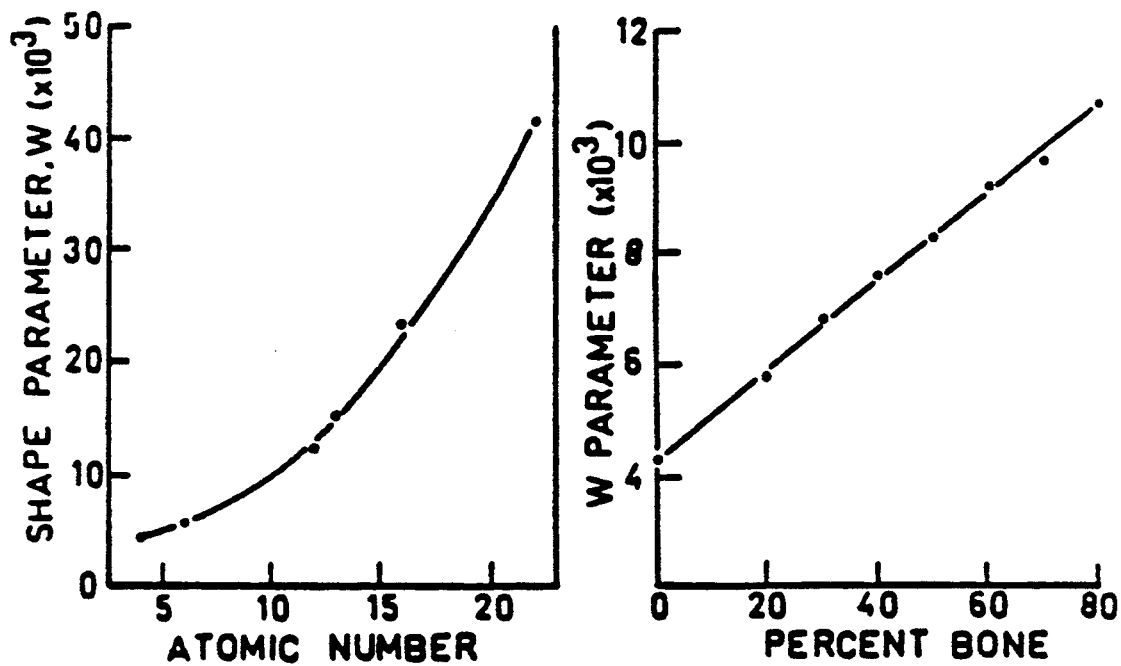
FIG. 2A  FIG. 2B

METHOD AND APPARATUS FOR LOW DOSE ESTIMATES OF BONE MINERALS IN VIVO GAMMA RAY BACKSCATTER

This is a division of application Ser. No. 07/762,326, filed on Sep. 18, 1991.

FIELD OF THE INVENTION

The present invention relates in general to a method and apparatus for estimating bone-mineral content and more particularly to an apparatus and method of monitoring osteoporosis.

BACKGROUND OF THE INVENTION

Prior art techniques for determining bone mineral content in vivo, by means of energy dispersive detectors, use analyses based on the relative areas under the peaks in pulse-height spectra. Examples of such prior art techniques are disclosed in an article by P. Tothill entitled Methods of Bone Mineral Measurement, Phys. Med. Biol. 1989; 34: 543–72.

SUMMARY OF THE INVENTION

According to the present invention, a method is provided for low-dose estimates of bone minerals based primarily on the shape rather than the intensity of the backscatter peak in pulse-height spectra.

According to an additional aspect of the invention, apparatus is provided for effecting the analysis of the present invention utilizing axially symmetric geometry which allows for the use of weak radiation sources, short measurement times and small doses of radiation.

According to an aspect of the present invention there is provided a method for obtaining low dose estimates of bone mineral in vivo, comprising the steps of irradiating a target with a low radiation dose, measuring backscatter radiation from said target using an NaI(TI) spectrometer for deriving a composite RaYleigh and Compton scattering peak representation of said backscatter radiation, and calculating a shape parameter W from said peak representation, as follows:

$$W = \int_{58}^{63} n(\epsilon)d(\epsilon) / \int_{35}^{67} n(\epsilon)d(\epsilon),$$

where $n(\epsilon)$ is the number of counts at energy $\epsilon$, and the integral limits are energies of radiation in keV, wherein said shape parameter W approximates a linear function of bone mineral content in vivo.

According to a further aspect of the invention there is provided a radioactive source holder for use with a NaI(TI) spectrometer for obtaining very low dose estimates in bone minerals in vivo, comprising a molybdenum tube, a gold insert within said tube, a blind hole within said insert for receiving the radioactive source, and an inner tube inserted into said blind hole for directing radiation from said source in a narrow cone, whereby said directing of radiation in said narrow cone minimizes spectrometer response to radiation which has been scattered by soft tissue overlying a bone.

BRIEF DESCRIPTION OF THE DRAWINGS

Aspects of the present invention will be further described with reference following drawings, in which:

FIG. 1B is a composite Compton and Rayleigh scattering profile measured with the backscatter spectrometer of FIG. 1A for sulphur and paraffin wax;

FIGS. 2A and 2B are graphs showing sensitivity of a shape parameter in accordance with an aspect of the invention on ideally homogeneous targets of elemental solids of low atomic number and uniform mixtures of powdered cortical bone and wax, respectively, FIG. 3 graphically illustrates test results of the shape parameter on inhomogeneous bones in vivo of a human patient.

DETAILED DESCRIPTION OF THE PREFERRED EMBODIMENTS

Figure 1A:
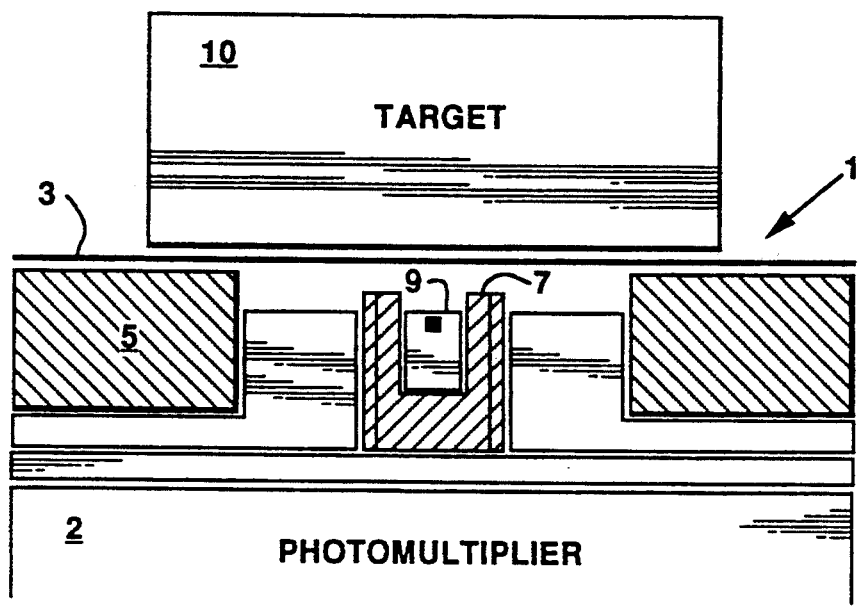
FIG. 1A is a longitudinal section to scale through the source-detector section of an axially symmetric backscatter spectrometer in accordance with the present invention.

A longitudinal section of the source-target-detector arrangement of the present invention is shown in FIG. 1A. The spectrometer uses a NaI(TI) X-ray scintillator which is evolved from a Ge backscatter spectrometer such as described in an article by the inventor entitled Nondestructive Analysis of Thick-Target Specimens by Gamma-Ray Backscatter appearing in the Canadian Journal of Physics, August 1989.

The spectrometer 1 comprises a photomultiplier detector 2 and a mylar sheet 3 (0.13 mm thick) attached by epoxy to an Sn fabricated iris 5, for preventing soft tissue from relaxing under pressure into the aperture of the iris 5 when the instrument is pressed firmly against the skin. A source holder 7 contains a commercially produced point source of radioactive material 9 such that radiation is directed toward a target specimen 10 through iris 5.

A simple demonstration of the principles underlying the design is shown in FIG. 1B where the backscatter peak for paraffin wax (dotted line) which is a simulant for soft tissue, is compared to the backscatter peak for sulphur (solid line). Sulphur is the only convenient solid which is close, in atomic number, to both phosphorus and calcium, the main mineral constituents of bone.

With a prior art Ge spectrometer, the peaks due to Rayleigh scattering (59.54 keV) and Compton scattering (48.8 keV), would be fully resolved, permitting analysis of mixtures on the basis of R/C ratios in a well known manner. The large contrast in width of the Compton profiles would also permit analysis by DuMond spectrometry such as described in the above-identified article by the inventor.

However, with lower priced NaI(TI) spectrometers the two peaks are mixed so that an R/C analysis is impractical. Nevertheless, the shape of the composite peak still has a strong Z dependence which can be exploited for a hybrid analysis of mixtures.

A useful shape parameter is defined by the fraction of the peak area in the interval of high contrast; for the wax sulphur combination, this becomes:

$$W = \int_{58}^{63} n(\epsilon)d(\epsilon) / \int_{35}^{67} n(\epsilon)d(\epsilon),$$

where $n(\epsilon)$ is the number of counts at energy $\epsilon$ and the limits of the integrals are the energies in keV.

Measurements on 3 cm thick specimens of Ba, C, Mg, Al, S and Ti utilizing the apparatus of the invention have established the Z dependence of the W parameter on solid, elementary targets as shown with the reference to FIGS. 2A and 2B. Uniform mixtures of powdered cortical bone in paraffin wax have shown that W is very nearly a linear function of bone content in ideal, homogeneous targets (FIG. 2B). Each of the runs depicted in FIGS. 2A and 2B lasted 100 seconds.

The sampled volume adjacent to the iris 5 of the spectrometer 1 is approximately cylindrical in shape, with maximum sensitivity at the surface and decreasing to half maximum at about 3 mm depth. Such a spatial dependence is clearly incompatible with probing such important bones as the lumbar vertebrae and the proximal femur. However, promising contrast and reproducibility has been found for several sites which are thought to be worthy of study, either because of convenience or sensitivity to osteoporosis.

Figure 3:
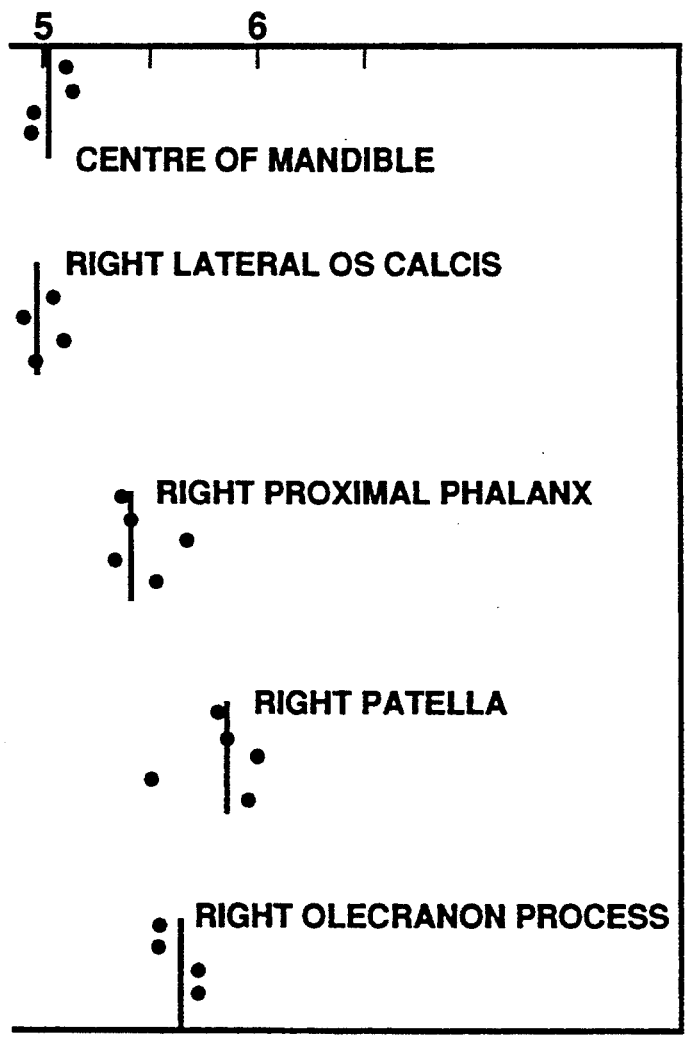

FIG. 3 shows multiple readings of W for runs of 20 seconds duration, of the centre of the mandible, the right lateral os calcis, the 2nd right proximal phalanx, the right patella and the right olecranon process of a human patient.

Experience shows that the W values do not follow a normal distribution when repeated measurements are made on one site—with the spectrometer 1 removed and repositioned manually after each reading. In view of this experience, it is thought to be advisable to use a resistant indicator of the W value and the use of the median of multiple readings is favoured over the more popular mean. The horizontal lines on FIG. 3 indicate the median for the groups of readings, each of 20 seconds duration.

Figure 4:
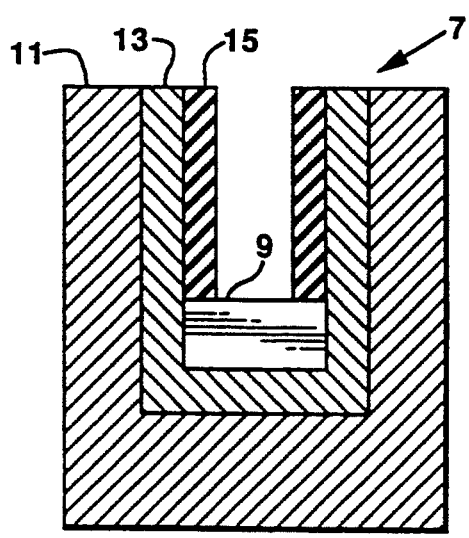
FIG. 4 is a detailed longitudinal section view of a modified radioactive source holder in accordance with a preferred embodiment of the present invention.

According to the preferred embodiment of FIG. 4, the source holder 7 is shown in cross section comprising a molybdenum tube 11 and a gold insert 13 having an aperture therein which forms a blind hole into which the radioactive source 9 may be placed. An inner tube 15 is then inserted into the blind hole of tube 13 such that the tube 15 directs the radiation from source 9 in the form of a narrow cone. The objective is to generate a "dead zone" above the source holder. The insert 15 is preferably fabricated from a dense metal such as gold.

When testing for osteoporosis in patients, it is desirable to minimize the response to radiation which has been scattered by the soft tissues that overlie the bone. Such scattering typically results in "background noise" that reduces the sensitivity to changes in bone-mineral content. By providing the insert 15 as shown in FIG. 4, the dead zone can be extended about 6 mm from the mouth of the holder 7 and beyond the patient's skin, tendons, etc. In that way, the signals that are recorded are produced almost entirely by scattering in the bone of interest.

The new design of source holder shown in FIG. 4 achieves the goal of having almost zero sensitivity to events in which the primary photon is scattered by material lying in the "dead zone", (i.e. in the first 6 mm. above the source holder 7). The result is that nearly all of the recorded data are produced by events in which the primary photons are scattered at depths of 6 mm or more into the "target". Normally, this means that the scattering occurs in bone rather than in overlying soft tissues such as skin, muscle, tendons etc.

However, the scattered photons must pass through that overlying tissue in order to reach the detector. In that process, some of the secondary photons will also be scattered in the soft tissue and this will have a small (but not negligible) effect on the shape of the combined Rayleigh and Compton peak. These changes would be misinterpreted as being due to a change in composition of the bone in the absence of any correction being made for the thickness of the overlying tissue.

Also, the thickness of overlying tissue has a small but not completely negligible effect on the geometric resolution of the system.

Hence, it is important to know how much soft tissue overlies the bone so that suitable corrections can be made to the shape parameters. The function of the $^{109}$Cd source is to provide an accurate estimate of that thickness.

The reason why $^{109}$Cd can provide this information is that is produces two types of radiation with markedly different absorption in bone. The higher-energy γ-ray at 88 keV produces a backscatter peak (at about 66 keV) which passes through bone with very little absorption. On the other hand, the 22 keV X-rays of Ag, which it also produces, generates a backscatter peak which is very readily absorbed in bone, but not in soft tissue. Because of these characteristics, a bone with a thick covering of soft tissue will produce a large ratio for the X-ray/γ-ray profile intensities. If the bone has only a thin covering of soft tissue, the ratio is very low. It is easy to detect differences of less than 0.5 mm from measuring this ratio.

It is important to note that the $^{109}$Cd source has to be in a holder 1 of the type shown in FIG. 1A and not the holder 7 of FIG. 4.

It should be noted that where repeated measurements are being taken at the same position on one patient it would not be necessary to introduce the complication of using $^{109}$Cd; One could simply make the same type of measurement repeatedly using a $^{231}$Am source and observe changes with time (or treatment). It is only when one wishes to compare readings at two distinctly different positions, or on different patients, that it becomes important to correct for overlying tissue.

Thus, according to the principles of the present invention, the depth of bone may be detected using a $^{109}$Cd source and the information detected thereby used to modify the W values determined with a $^{241}$Am source, thus allowing for inhomogeneity of the system.

Other embodiments and modifications of the invention are possible within the sphere and scope as defined in the claims appended hereto.

I claim:

1. A method for obtaining low dose estimates of bone mineral content in vivo, comprising the steps of irradiating a target bone mineral with a low radiation dose, measuring backscatter radiation from said target bone mineral using an NaI (TI) spectrometer for deriving a composite Rayleigh and Compton scattering peak representation of said backscatter radiation, and calculating a shapes parameter W from said peak representation, as follows:

$$W = \int_{58}^{63} n(\epsilon)d(\epsilon) / \int_{35}^{67} n(\epsilon)d(\epsilon),$$

where $n(\epsilon)$ is the number of counts at energy $\epsilon$, and the integral limits are energies of radiation in keV, and wherein said shape parameter W approximates a linear function of an estimate of the bone mineral content in vivo.

2. The method of claim 1 wherein said low radiation dose is a source of $^{109}$Cd.

3. The method of claim 1 wherein said low radiation dose is a source of $^{241}$Am.

4. A radioactive source holder for use with a NaI (tI) spectrometer for obtaining very low dose estimates of bone minerals in vivo irradiated from a radioactive source adapted to be placed in said holder, said holder comprising a molybdenum tube, a gold insert within said tube, a blind hole within said insert adapted to receive radioactive source, and an inner tube inserted into said blind hole for directing radiation from the radioactive source in a narrow cone, whereby said directing of radiation in said narrow cone minimizes spectrometer response to radiation which has been scattered by soft tissue overlying a bone.

5. The radioactive source holder of claim 4 wherein said inner tube is fabricated from a dense metal.

6. The radioactive source holder of claim 5 wherein said dense metal is gold.

7. A radioactive device for use with a NaI (tI) spectrometer for obtaining very low dose estimates of bone minerals in vivo irradiated from said said holder comprising a molybdenum tube, a gold insert within said tube, a blind hole within said insert receiving said radioactive source, and an inner tube inserted into said blind hole for directing radiation from said radioactive source in a narrow cone, whereby said directing of radiation in said narrow cone minimizes spectrometer response to radiation which has been scattered by soft tissue overlying a bone and said radioactive source is $^{241}$Am.

* * * * *